United States Patent [19]
Korol et al.

[11] Patent Number: 4,857,334
[45] Date of Patent: Aug. 15, 1989

[54] SYNTHETIC RESIN MATRIX SYSTEM INCORPORATING HEALING ENHANCER

[75] Inventors: Bernard Korol, Highland Beach, Fla.; Paul Nathan, Cincinnati, Ohio

[73] Assignee: Enquay Pharmaceutical Associates, Boca Raton, Fla.

[21] Appl. No.: 199,375

[22] Filed: May 27, 1988

Related U.S. Application Data

[63] Continuation-in-part of Ser. No. 815,874, Jan. 3, 1986, Pat. No. 4,747,845, which is a continuation-in-part of Ser. No. 542,754, Oct. 17, 1983, Pat. No. 4,563,184.

[51] Int. Cl.$^4$ ............................................. A61L 15/00
[52] U.S. Cl. ........................................ 424/445; 424/81; 424/446; 424/486; 424/487
[58] Field of Search ............... 424/445, 446, 487, 484, 424/486, 81, 78; 523/111; 128/156, 155

[56] References Cited

U.S. PATENT DOCUMENTS

| | | | |
|---|---|---|---|
| 3,287,222 | 11/1966 | Larde et al. | 424/445 |
| 3,419,006 | 12/1968 | King | 424/445 X |
| 4,191,743 | 3/1980 | Klemm et al. | 424/445 |
| 4,272,518 | 6/1981 | Moro et al. | 424/81 |
| 4,347,841 | 9/1982 | Benyo et al. | 424/445 X |

FOREIGN PATENT DOCUMENTS 0041934 12/1981 European Pat. Off. ............ 424/445
2725261 12/1978 Fed. Rep. of Germany ...... 424/445

Primary Examiner—Thurman K. Page

[57] ABSTRACT

An apparatus and method is described for applying epidermal growth factor (EGF) for achieving healing enhancement at a wound site. The human source of epidermal growth factor, designated as hEGF, is applied from the synthetic resin matrix system of this invention, and which comprises a polymer, such as poly(2-hydroxyl ethyl methyl methacrylate), referred to as PHEMA, an organic solvent, such as polyethylene glycol (PEG), and a hydrogen binding plasticizer, such as dimethylsulfoxide (DMSO). The plasticizer regulates the set-up time of the synthetic resin, so that the more plasticizer present, the shorter the set-up time. The dressing, once formed, and having the healing enhancer contained therein, may be sealed within various backing sheets, in order to preserve its aseptic condition. When ready for use, one of the backing sheets may be peeled away to expose the resin pad with the embodied healing enhancer, ready for application to the wound site.

6 Claims, 1 Drawing Sheet

U.S. Patent
Aug. 15, 1989
4,857,334
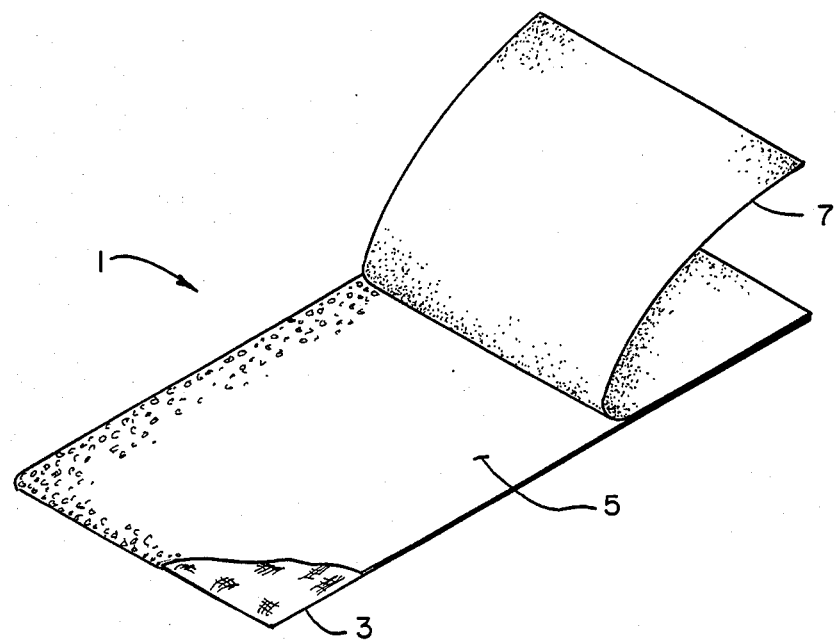
FIG.I.
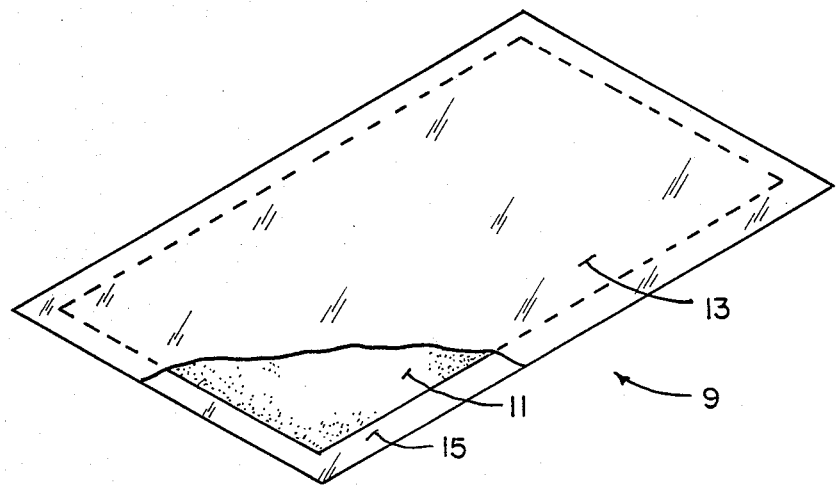
FIG.2.

SYNTHETIC RESIN MATRIX SYSTEM INCORPORATING HEALING ENHANCER

CROSS-REFERENCE TO RELATED APPLICATIONS

This application is a continuation-in-part of the patent application of Bernard Korol, Ser. No. 815,874, filed on Jan. 3, 1986, now U.S. Pat. No. 4,747,845 and which application is denominated as a continuation-in-part of the patent application of Bernard Korol, Ser. No. 542,754, filed on Oct. 17, 1983, and now U.S. Pat. No. 4,563,184, all of which applications and patent are owned by a common assignee.

BACKGROUND OF THE INVENTION

This invention relates to a synthetic resin matrix system which can be embodied with select drugs and chemicals, in this particular instance, healing enhancers, and provide a suitable storage for the extended and sustained duration release of the embodied enhancer from the matrix system following various modes of administration.

According to the literature, such as in Madan, Pharmaceutical Manufacturing, April, 1985, approximately fifty major pharmaceutical companies are engaged in the production and marketing of about two hundred sustained-release drug delivery products, which represent about 5% of the total pharmaceutical products sold. This survery of literature shows that various methods have been used to fabricate these drug products. Most of the methods develop a series of protective layers of inert substance which encapsulate the drug and utilize dissolution as the rate-limiting step in controlling the release of the active ingredient from the dosage form. Because a drug form with a low dissolution rate of the overlayer is slowy released, the main thrust of the development of sustained-release delivery systems has been directed towards drugs that are highly water soluble. However, the solubility of such drugs can be changed by several methods.

In addition, in the treatment of wounds, and which may be provided for the sustained release of medicament from a dressing to the wound, such applications are available in the prior art, but most of such applications become too hard after setting in place, after application from the paste form, and do not effectively incorporate sufficient elasticity and flexibility in their structure, so as to function effectively as a dressing that may be applied, in the bandage form, over a wound surface, in order to aid in the enhancing of wound healing, as from a burn, or any other wounds. One such in situ plastic wound bandage is disclosed in U.S. Pat. No. 4,272,518, to Moro, et al, which is a settable paste contains a polymer, and an inert, normally liquid solvent. While this plastic wound bandage paste worked well for its intended purpose, in that a non-tacky, homogeneous, occlusive film was formed on the surface of the wound, relative long and unpredictable set-up times, in some instances as long as an hour, resulted when useful ratios of solvent vis-a-vis the polymer were mixed. Also, in many instances, the resuting film bandage formed on the wound site became brittle and was subject to cracking or splitting, especially upon movement of the patient, thus rendering the plastic film substantially ineffective as a barrier against personnel, patient, or environmentally transmitted bacteria and the like.

In view of the foregoing, the current invention incorporates the synthetic resin matrix system as defined in this invention, and so as adequately described in the parent applications from which this application derives, so as to provide a very effective plasticizing type of bandage, that can incorporate various healing enhancers, can be applied directly to a wound site, and in most instances, as the examples will review, accelerates the wound healing process.

SUMMARY OF THE INVENTION

The synthetic resin matrix system of the parent inventions (See U.S. Pat. No. 4,563,184, and the application having Ser. No. 815,874) has been given the acronym "DIMAC", which represents the chemical components of the drug carrier and delivery system, comprised of a particulate, hydrophillic, water swellable polymer, an inert, non-toxic water miscible organic solvent, and a hydrogen bonding plasticizer, having the active drug, in this particular instance, a healing enhancer, embedded within and throughout the matrix by the adding of the drug to it while mixing of the dressing components. The potential of DIMAC to serve as a matrix for drug storage and drug delivery, in this instance for the delivery of a healing enhancer, whether it be by an initial primary delivery, or a sustained release, was realized by the chance observation that the addition of the hydrogen bonding plasticizer, dimethysulfoxide, or equivalent ingredients, to the formulation containing only the polymer, poly(2-hydroxyethylmethacralate), and the organic solvent, polyethylene glycol-400, produce a synthetic polymer matrix system which exhibits essential and significant improvements in physical and functional characteristics over prior related products. The added solvent may have a molecular weight of between 200 to 2000 grams molecular weight units. The DIMAC was shown to release the embodied enhancer in an extended duration pattern.

DIMAC, incorporating various epidermal growth factors, in order to enhance in the contraction and epithelialization of surface wounds, during testing, worked quite effectively in stimulating the more rapid healing of any such impairment. The preparations were effective in enhancing the treatment and healing of the injury. Just as important, the DIMAC system of this current invention, incorporating the healing enhancer, may likewise incorporate some of the other drugs as identified in the parent application and patent, in order to likewise act as a bacterial barrier to prevent bacterial contamination of the wound site, during its accelerated healing.

Healing enhancement, that is the contraction and epithelialization of surface wounds in a significantly shortened period of time without associated deleterious effects, can be facilitated with the use of these epidermal growth factors (EGF). The human sources of epidermal growth factor designated as hEGF, particularly saliva, blood elements, such as macrophages and platlets, and other cells such as keratinocytes and fribroblasts were used to isolate hEGF. This hEGF was subsequently subjected to structural analysis and was identified as a polypeptide containing 53-amino acids and having a molecular weight of approximately 5000 gram molecular weight units. As a result of new technology, this human derived epidermal growth factor (hEGF) can be obtained in sufficient supply from recombinant DNA sources for evaluation and use as a healing enhancer in humans. A source of such ingredient is Chiron Corp., of Emeryville, Calif. 94608, and is obtained under the brand name "hEGF".

Animal and human studies have been performed examining the effectiveness of hEGF in enhancing the healing of partial thickness wounds. In guinea pigs, investigation of the rate of donor site epithelialization has been undertaken following a dermatome-induced surface wound having a wound depth of 0.005 inch (0.125 mm) and 0.010 inch. The wound size was 3 cm square. The wounds were made on each side of the dorsum of the guinea pig. Three groups of guinea pigs, each group containing 8 animals (16 wounds), were tested for each wound depth. These groups were designated as Group I, II, and III. Group I received 10 ugm/cm square of hEGF applied daily in solution to the wound site and covered with an inert gel. Treatment continued for seven days. Group II animals were the positive controls and were treated only with the inert gel applied daily for seven days. Group III guinea pigs remained untreated and served as the negative controls. Wound size was measure daily at the time of dressing change, and biopsies and photographs of the wound were obtained on days 1, 3, and 7. On day 7, the wounds were excised and following the removal of the dermis, the amount of epithelialization in the epidermis was measured directly. The results revealed that treatment with hEGF approximately doubled the rate of wound closure in both the 0.005 and 0.010 inch wound depths at the first 3 days treatment. In the following 4 days, the rate of healing in the treated wounds somewhat slowed but remained in excess of the control. The histophathological examination of the regenerating epidermis supported the macroscopic findings of accelerated epithelialization on day 3 in the hEGF treated wounds. It was concluded that human epidermal growth factor, produced by recombinant DNA procedures, is effective in increasing the rate of epithelial proliferation and thereby enhances the healing of partial thickness surface wounds in guinea pigs. (Reference: Effect OF Human Epidermal Growth Factor On The Rate Of Donor Site Reepithelialization In Guinea Pigs, Vakili, Cyrus, Jung, Walter K. and Burke, John F., Abstract #11, Proceedings Of The American Burn Association Twentieth Annual Meeting, Mar. 23-26, 1988, Seattle, Wash.)

In patients requiring split-thickness grafting for the treatment of burns or other reasons, one of each pair of donor sites created with a dermatome set at 12/1000 inch was treated topically with Silvadene Cream or with Silvadene Cream contaning 10 ugms/ml of human epidermal growth factor (hEGR). As was the case in the aforementioned guinea pig study, hEGF was identified as a 53-amino acid polypeptide prepared from recombinant DNA sources that was shown in animal studies to accelerate epithelialization of partial-thickness wounds. In this human study, each patient served as their own control, receiving the respective treatment applied twice daily at the does of 0.5 ml/cm. square per one centimeter square wound. Daily photographs of the wound sites were analyzed by computerized planimetry to determine the percentage of epithelialization of each wound each day. It was found in 14 of the 15 patients that wounds treated with Silvadene Cream containing hEGF were resurfaced with epithelial cells before the Silvadene Cream control treated wounds. Furthermore, the histological morphometric analysis of the 4 ml punch biopsies, obtained form each wound on treatment day 5, revealed that the wounds treated with hEGF in Silvadene Cream exhibited a thicker, more differentiated epidermis than the wounds treated with Silvadene Cream alone. (Reference: Human Epidermal Growth Factor Enhances Donor Site Healing In Man. Brown, G. L., Nanney, L. B., Griffin, J., Cramer, A., Schulta, G. S., Jurkiewicz, M. J., and Lynch, J. B., Abstract #10, Proceedings Of The American Burn Association Twentieth Annual Meeting, Mar. 23-26, 1988, Seattle, Wash.

The designation, DIMAC, is an acronym for a polymer matrix system exhibiting a special capability to store and deliver many different chemical or pharmacological agents in a most desireable extended duration pattern of release. One of the early products to contain DIMAC is intended to be an antimicrobial product incorporating silver sulfadiazine. The unique capability of DIMAC matrix to serve as a storage site and to provide extended duration delivery of the embodied silver sulfadiazine over days, will eliminate the requirement for once-or-twice-a day wound dressing changes, to dressing changes usually no more often than every 4-5 days. This special quality of DIMAC matrix warranted the performance of preliminary studies examining the efficacy of DIMAC matrix to serve as a storage and extended duration delivery system for human epidermal growth factor. The "SILDIMAC" Wound Dressing, containing silver sulfadiazine, was used as the format design for these DIMAC/hEGF storage and extended duration release studies. The formulation of DIMAC/hEGF employed in these studies had the following wt % components:

PHEMA: 35% PEG-400: 60% DMSO:3.995% hEGF 0.005% The dressing was comprised of one (1), the peel-throw-away olefin cover; (2), the DIMAC polymer matrix containing embodied hEGF; and (3), the nylon-lycra biaxially stretchable support system laminate to the DIMAC polymer matrix. The DIMAC matrix had a thickness of 0.375 millimeters. Samples of fixed sizes and weights of DIMAC/hEGF were placed into an extraction chamber containing 2 cc saline. After 1-hour, the sample was removed from the chamber and placed into a new chamber containing a fresh supply of saline. This procedure was repeated for 7-transfers (8-hours). The eight chamber saline samples were assessed for concentration of hEGF using conventional protein analytical procedures. It was observed that hEGF did leave the DIMAC matrix in a pattern akin to a first order rate of release with 80% of the embodied hEGF released by the 6-hour extraction interval. Furthermore, it was calculated that 100% of the embodied material was released by the end of the eight hour extraction period.

These findings were examined further in a study employing an identical saline extraction procedure but using a bioassay procedure to determine influence of the stored and released hEGF on the rate of epithelial cell proliferation. The criteria for effective hEGF activity was based upon the capability of hEGF to stimulate the rate of human epithelial cell proliferation, in a tissue culture procedure, by multiples up to 200%. The results revealed on absolute concordance between the chemical analyses and the proliferation bioassay findings at all sampling timesfand for all levels of hEGF concentrations in the saline extracts from the DIMAC/hEGF samples.

It was concluded from these studies that DIMAC matrix is an appropriate storage system for the 53-amino acid polypeptide, hEGF (M.W. approximately 5000 gram molecular weight units), and that when placed in an aqueous environment, the DIMAC matrix provides for an extended duration delivery of the embodied hEGF without altering the increased epithelial cell proliferation bioeffectiveness of the released polypeptide.

Earlier studies supported the premise that drug release from DIMAC matrix is primarily controlled by the nature of the surroundings in contact with the DIMAC/drug system. In-vitro and in-vivo studies were performed on DIMAC/drug formulations prepared in the configuration of a wound dressing. It was observed that the drug release from the DIMAC matrix is facilitated by an aqueous environment. The application of the DIMAC/drug wound dressing to wound sites, agar, or cadaveric skin, revealed further that the amount and duration of drug release from the DIMAC matrix was dependent upon the relative concentration of the drug in the DIMAC matrix and the thickness of the matrix layer. DIMAX matrix is an anhydrous hydrophilic system which, when placed upon or into an aqueous location, readily takes up water in exchange for the formulated polyethylene glycol containing the solubilized inclusionary drug agents or polypeptides. This proposed mechanism of bidirectional diffusion by which DIMAC matrix provides extended duration release of embodied agents also explains the sustained release of hEGF from DIMAC/hEGF samples.

Other formulations containing the components, as used in the study described here, have been presented in the identified continuation-in-part patent application, Ser. No. 815,874, as aforesaid, and would also be efficacious storage and delivery systems for healing enhancers.

BRIEF DESCRIPTION OF THE DRAWINGS

In referring to the drawings, FIG. 1 discloses in perspective view a preformed wound or other type of dressing of the present invention incorporating the epidermal growth factor, as an ngredient in the polymer coating, as it is applied to a wounded surface, such as the surface of the skin of a human or animal, and with a backing sheet covering the dressing material and showing it in a partially peeled-away condition.

FIG. 2 is a perspective view of a preformed wound dressing of the present invention sheathed between two backing sheets, having transparency, with the wound dressing and backing sheets being such to facilitate wound observance.

DESCRIPTION OF THE PREFERRED EMBODIMENT

Generally, the synthetic wound dressing, and containing the ingredient of a healing enhancer of the present invention, comprises a resin of varying concentrations of biologically compatible, non-toxic, hydrophilic, water insoluble, water swellable polymer, such as those as listed in this application. The polymer of this invention may include hydroxy($C_2$–$C_4$-alkyl) methacrylate, hydroxy($C_2$–$C_4$alkyl) acrylate, hydroxy($C_2$–$C_4$alkoxy$C_2$–$C_4$alkyl) methacrylate, hydroxy($C_2$–$C_4$alkoxy$C_2$–$C_4$alkyl) acrylate, alkoxy($C_2$–$C_4$alkoxy$C_2$–$C_4$alkyl) methacrylate, alkoxy($C_2$–$C_4$alkoxy$C_2$–$C_4$alkyl)acrylate, N-($C_1$–$C_4$alkyl) acrylamide, N$C_1$–$C_4$alkyl) methacrylamide, N,N-di($C_1$–$C_4$alkyl) acrylamide, N,N-di($C_1$–$C_4$alkyl) methacrylamide, vicinal-eopxy($C_1$–$C_4$alkyl) methacrylate, or vicinal-epoxy($C_1$–$C_4$alkyl) acrylate. This component is generally referred to as PHEMA.

Additionally, the resin comprises an inert, water soluble, organic liquid solvent, previously generally identified as PEG. This ingredient may be selected from the group consisting of polytheylene glycol or polypropelene glycol having a molecular weight averaging between about 200 to 2000 grams molecular weight units. A hydrogen bonding plasticizer additive, such as dimethylsulfoxide, is also included, and was previously referred to as the DMSO ingredient. It has been found that the formulation of the resin of this inventin, consisting essentially of PHEMA, PEG, and DMSO, and referred to collectively as DIMAC, can be altered so as to control the set-up time of the resin from almost simultaneous with mixing (e.g. several seconds) up to about 45 minutes, or longer, depending upon the relative concentration of the ingredient DMSO. Where this composition is to be used as a wound dressing, for providing healing enhancement, for application to the surface to the human body, or that of an animal, or the like, the dressing bandage in an already adherent state is applied to the body, rather than as a spreadable paste. More specifically, in referring to FIG. 1, the preformed dressing is illustrated in its entirety by the reference character 1. This preformed dressing then is shown to comprise a substrate 3, preferably of a biaxially stretchable fabric-like material. For example, such a bidirectional stretchable material made of nylon or Lycra is available from Tweave, Inc., of Norton, Mass., under the trade designation or style No. 901. A layer of the stretchable wound dressing 1 of the present invention is applied to the front face of the substrate 3 with the layer of the synthetic wound or other form of dressing being indicated by the reference character 5. This includes the DIMAC ingredients as listed above. In this particular instance, the dressing will include the addition of the healing enhancer, which incorporates the epidermal growth factor, as previously summarized, and which will be applied in the concentration as previously disclosed with respect to the examples of usage of this particular invention. On the other hand, it is just as likely that the hEGF can be used at very minimal amounts, as low as 0.001%, by weight, of the composition, up to approximately 1% by weight. To protect the dressing coating 5 applied to substrate 3 prior to usage, and to maintain it in an aseptic condition, a plastic film backing sheet 7 is applied to the synthetic wound dressing coating 5, and is lightly adhered to substrate 3. As shown in FIG. 1, prior to usage, the backing sheet 7 is peeled away from the dressing so as to expose the dressing coating 5 on the substrate 3, thus making the bandage or dressing ready for application to the skin and wound surface, for providing healing enhancement, as described. Substrates 3 and 7 may extend beyond the wound dressing 5 to provide a non-adhesive tab permitting easy handling of the dressing after removal of the cover film 7 without touching the active sticky surface 5 of the medicament ingredient.

While the description of the formulation of the ingredients of this dresssing has already been described in detail, in the summary of this invention where examples of usage and application have been analyzed, it must be recognized that there are variations to the amount of ingredients that may be utilized. For example, the polymer may be used ranging between about 30% to 55% by weight of the dressing. The solvent application ranges between about 20% to 60% by weight of said dressing. And, the plasticizer is present within the composition in an amount ranging to about 20% by weight of said dresssing. These are the preferred ingredient ranges, in the mixing and forming of the dressing, for use in combination with the healing enhancer identified herein.

While the inclusion of the DMSO plasticizer as a component of the formulation of the synthetic esin dressing of the present invention has heretofore been described as primarily aiding in giving predictability to the set-up time of the synthetic resin dressing, it has been found, even in the case of the preformed dressing bandages, such as shown in FIG. 1, that the inclusion of DMSO (or other plasticizers) as a component of the formulation for the synthetic resin wound dressing coating 5 on the bandage, has a beneficial effect in that it is believed that the DMSO plasticizer results in a solidification or curing of the polymer system of the synthetic resin dressing such that there is a progressive gelling of the resin mixture following the actual set-up of the mixture. The term "set-up" is defined as the time between the mixing of the components of the synthetic resin wound dressing into a paste and the time and occlusive, non-tacky film appears on the surface of the paste with little or no adhesiveness to the touch. Generally, at the time of set-up, the resin will still have a pliable consistancy. When no drug or medicament has been added, the paste in its "set-up" condition will have semi-opaque character.

Then, depending on the relative concentration of the components of the synthetic resin system, a progressively developing transparency of the resin film will result with an increase in the elasticity and rebound of the resin, and the surface of the resin will generally have a significantly increased surface adhesiveness resulting from the reactions of the added DMSO. Generally, these last-described changes and physical characteristics of the resin system require about five to ten times longer to develop than is required for the initial "set-up" to occur. This delay process of developing a transparent film with an increase in elasticity, rebound and surface adhesiveness is referred to as "curing."

The various polymers utilized in the fabrication of this invention have already been analyzed above. The solvent utilized within this invention may comprise a polyethylene glycol or polypropylene glycol, as aforesaid, and preferably having a molecular weight between about 200–2000 gram molecular weight units. In addition, it is likely in lieu of dimethylsulfoxide, that equivalent type compounds may be used to provide the desired elasticity to the finished product, and therefore, the plasticizer applied in this invention may be selected from the group of dimethylsulfoxide, dimethylphthalate, 2,3-butylene carbonate, dimethylformamide, dimethyltetramethylene sulfone, dimethylsulfone, methylene glycolate, methylpropyl sulfone, or butyrolactone.

When the healing enhancer, comprising the epidermal growth fractor (EGF), with the DIMAC composition, is applied to the surface of the substrate 3, it may be included within the DIMAC, the carrier material, so as to provide for its adherence to the surface of the substrate, and to remain thereon, even as the plastic film backing sheet 7 may be in the process of removal.

FIG. 2 shows another embodiment of the preformed synthetic resin wound dresssing of the present invention, and as indicated in its entirety by reference character 9. More specifically, the wound dressing 9 comprises a pad 11 of the synthetic resin of this invention (i.e., DIMAC) including the healing enhancer ingredient, of a predetermined thickness (eg. 0.5 to 1.0 mm). The pad is covered by upper and lower backing sheets 13 and 15, respectively, of thin, transparent plastic film sealed around their margins so as to maintain the pad in an aseptic condition. In use, one of the backing sheets may be peeled from the DIMAC matrix pad 11 so as to expose a surface of the pad, to which the epidermal growth factor composition, as summarized herein, will have been previously intermixed in its required amount. Because the pad and the remaining backing sheet are transparent, the clinician may visually observe the wound site through the pad without the requirement of having to remove the wound dressing and thus violating the microbial barrier provided by the said dressing.

Variations or modifications to the subject matter of this disclosure may occur to those skilled in the art upon reviewing the summary and description of this invention. Such variations and modifications, if within the spirit of this invention, are intended to be encompassed within the scope of any claims to patent protection issuing upon this invention. The description of the preferred embodiments set forth is done so principally for illustrative purposes only.

. Having thus described the invention what is claimed and desired to be secured by Lettes Patent is:

1. A synthetic resin matrix system for drug storage and extended duration drug release comprising a particulate, hydrophilic, water swellable polymer, and inert, non-toxic water miscible organic solvent, and a hydrogen bonding plasticizer; said polymer selected from the group consisting of a synthetic resin matrix system for drug storage and extended duration drug release comprising a particulate, hydrophilic, water swellable polymer, an inert, non-toxic water miscible organic solvent, and a hydrogen bonding plasticizer, said polymer selected from the group consisting of hydroxy($C_2$–$_4$alkyl) methacrylate, hydroxy($C_2$–$_4$alkyl) acrylate, hydroxy($C_2$–$_4$alkoxy$C_2$–$_4$alkyl) methacrylate, hydroxy($C_2$–$_4$alkoxy$C_2$–$_5$alkyl) acrylate, alkoxy($C_2$–$_4$alkoxy$C_2$–$_4$alkyl) methacrylate, alkoxy($C_2$–$_4$alkoxy$C_2$–$_4$alkyl)acrylate, N-($C_1$–$_4$alkyl) acrylamide, N-($C_1$–$_4$alkyl) methacrylamide, N,N-di($C_1$–$_4$alkyl) acrylamide, N,N-di($C_1$–$_4$alkyl) methacrylamide, vicinal-epoxy($C_1$–$_4$alkyl) methacrylate, or vicinal-epoxy($C_1$–$_4$alkyl) acrylate, said solvent selected from the group consisting of polyethylene glycol or polypropylene glycol having a molecular weight averaging between about 200–2000 gram molecular weight units, and wherein said plasticizer being selected from the group consisting of dimethylsulfoxide, dimethylphthalate, 2,3-butylene carbonate, dimethylformamide, dimethyltetramethylene sulfone, diethylsulfone, methylene glycolate, methylpropyl sulfone, or butyrolactone, with said polymer ranging between about 15%–50% by weight of said matrix system, with said solvent ranging between about 30%–65% by weight of said matrix system, with said plasticizer ranging up to about 20% by weight of said matrix system, and further including a medicament agent for local or systemic therapeutic effects, said medicament agent being a growth factor or healing enhancer.

2. The invention of claim 1 and wherein said healing enhancer is an epidermal growth factor (EGF).

3. The invention of claim 2 and wherein said EGF is equivalent to human derived material (hEGF) comprising a polypeptide containing 53-amino acids and having a molecular weight of approximately 5,000 gram molecular weight units.

4. The invention of claim 3 and including a pair of backing sheets, and said matrix system with healing enhancer being arranged intermediate said sheets.

5. The invention of claim 4 and wherein said sheets being transparent.

6. The invention of claim 4 and wherein one of said backing sheets being elastic.

* * * * *

UNITED STATES PATENT AND TRADEMARK OFFICE
CERTIFICATE OF CORRECTION

PATENT NO.  : 4,857,334
DATED       : August 15, 1989
INVENTOR(S) : Bernard Korol, et al.

It is certified that error appears in the above—identified patent and that said Letters Patent is hereby corrected as shown below:

Column 8, line 31, claim 1, delete beginning with "hydroxy" through line 38 ending with "solvent", and susstitute the following:

-- hydroxy($C_2$-$C_4$-alkyl) methacrylate, hydroxy($C_2$-$C_4$alkyl) acrylate, hydroxy($C_2$-$C_4$alkoxy$C_2$-$C_4$alkyl) methacrylate, hydroxy($C_2$-$C_4$alkoxy$C_2$-$C_4$alkyl) acrylate, alkoxy($C_2$-$C_4$alkoxy$C_2$-$C_4$alkyl) methacrylate, alkoxy($C_2$-$C_4$alkoxy$C_2$-$C_4$alkyl) acrylate, N-($C_1$-$C_4$alkyl) acrylamide, N-($C_1$-$C_4$alkyl) methacrylamide, N,N-di($C_1$-$C_4$alkyl) acrylamide, N,N-di($C_1$-$C_4$alkyl) methacrylamide, vicinal-epoxy($C_1$-$C_4$alkyl) methacrylate, or vicinal-epoxy($C_1$-$C_4$alkyl) acrylate, said solvent --.

Signed and Sealed this

Ninth Day of October, 1990

*Attest:*

HARRY F. MANBECK, JR.

*Attesting Officer*        *Commissioner of Patents and Trademarks*